United States Patent [19] [11] Patent Number: 5,019,359
Kutner et al. [45] Date of Patent: May 28, 1991

[54] METHOD AND APPARATUS FOR RAPID STERILIZATION OF MATERIAL

[75] Inventors: Barry S. Kutner, Wilton; Daniel A. Latowicki, Newton, both of Conn.

[73] Assignee: Flexiclave, Inc., Del.

[21] Appl. No.: 440,793

[22] Filed: Nov. 22, 1989

Related U.S. Application Data

[63] Continuation-in-part of Ser. No. 274,768, Nov. 22, 1988, which is a continuation-in-part of Ser. No. 184,246, Apr. 21, 1988.

[51] Int. Cl.$^5$ .................................................. A61L 2/12
[52] U.S. Cl. ............................ 422/294; 219/10.55 E; 250/455.1; 422/21; 422/299
[58] Field of Search ................ 219/10.55 E; 422/21, 422/22, 28, 32, 33, 294, 288, 299, 305; 250/455.1; 426/107, 243, 234

[56] References Cited

U.S. PATENT DOCUMENTS

| | | | |
|---|---|---|---|
| 3,490,580 | 1/1970 | Brumfield et al. | 219/10.55 E |
| 4,015,085 | 3/1977 | Woods | 219/10.55 E |
| 4,196,331 | 4/1980 | Leveckis et al. | 219/10.55 E |
| 4,204,105 | 5/1980 | Leveckis et al. | 219/10.55 E |
| 4,514,497 | 4/1985 | Kit et al. | 435/235 |
| 4,865,921 | 9/1989 | Hollenberg et al. | 219/10.55 E |
| 4,878,765 | 11/1989 | Watkins et al. | 219/10.55 E |

Primary Examiner—Robert J. Warden
Assistant Examiner—Timothy M. McMahon
Attorney, Agent, or Firm—Steinberg & Raskin

[57] ABSTRACT

Method and apparatus for rapidly sterilizing material including articles such as dental handpieces include introducing the article and liquid sterilant solution into a collapsible pouch formed of vapor-impermeable sheet material, sealing the collapsible pouch to form a gas-tight assembly, and vaporizing the liquid sterilant solution by heating it to produce an atmosphere of hot sterilant vapor. The liquid sterilant is introduced into the pouch in a quantity sufficient to create an overpressure when vaporized which is indicated by the collapsible pouch expanding to a distended condition. In one embodiment, the liquid sterilant solution is vaporized by irradiating the gas-tight assembly with microwave radiation in which case the material is sterilized under the combined effects of chemical vapor and microwave irradiation. In other embodiments particularly suited for sterilizing material comprising a plurality of articles, the at least one article is surrounded by shielding, which may be separate from or integrated with the pouch, and which may be provided on or in, i.e. as part of, the sheet material forming the pouch, which presents a barrier to the transmission of microwave radiation. The pouch containing the shielded article or articles and liquid sterilant is sealed and the gas-tight assembly is irradiated with microwave radiation to vaporize the sterilant whereupon the article or articles are sterilized under the effect of chemical vapor.

35 Claims, 8 Drawing Sheets

METHOD AND APPARATUS FOR RAPID STERILIZATION OF MATERIAL

BACKGROUND OF THE INVENTION

This is a continuation-in-part of application Ser. No. 274,768 filed Nov. 22, 1988, which is a continuation-in-part of application Ser. No. 184,246 filed Apr. 21, 1988.

This invention relates generally to methods and apparatus for sterilizing material, and more particularly, to methods and apparatus for sterilizing material, such as dental and other medical instruments, in a rapid manner.

The need for effective sterilization of dental instruments, such as dental handpieces, is more important today than ever before due to the realization of the significant potential for infection via dental procedures and the increase in the rate of transmission of serious diseases by blood and saliva. However, from a practical viewpoint, not only must the sterilization procedure be effective, it must also be rapid, i.e., have a short turn-around or cycle time. Thus, it will be understood that the quantity of any one instrument that a practitioner or institution must purchase and have available for use will depend on the frequency of treatments requiring that instrument and on the turn-around time required to sterilize the instrument. In the case of dental handpieces, which generally are required for most treatments performed in the dental operatory, an extended sterilization cycle means that a larger inventory of available handpieces must be maintained. The high cost of dental handpieces, on the other hand, often limits the number of available handpieces, which in turn may result in hasty and therefore ineffective attempts at, or even dispensing with, lengthy sterilization procedures. This of course is unacceptable.

Heat sterilization methods, such as steam heat (autoclave), dry heat, and chemical vapor, are generally preferred over cold immersion methods, which are generally not effective unless glutaraldehyde is used and the instrument is immersed for 7–10 hours. Chemical vapor sterilization has the advantages of minimal corrosion of burs and other sharp instruments (steam sterilization or immersion in most liquid disinfectants produces dullness and rusting) and a cycle time which is relatively short compared to cold sterilization techniques.

One type of chemical vapor sterilizer which is in commercial use (available from MDT Corporation of Gardena, California under the designation Harvey Chemiclave) comprises a sterilizer which uses moderate heat (about 270° F.), pressure (about 20 psi) and a special solution composed primarily of 3A alcohol (about 80%) and water (about 9%) with small amounts of acetone, ketone and formaldehyde. The sterilization time is about 20 minutes after proper pressure is reached. The length of time required to reach pressure depends on the size of the load. On the other hand, the purchase price of this arrangement is higher than steam and dry heat processors. Additional drawbacks are that relatively large quantities of sterilizing solution are required, and odor and minor irritation of eyes, nose and throat from chemical vapors often accompanies use, the sterilizing chamber must be cleaned on a frequent basis, the instruments should be Wrapped to preserve sterility, and the simultaneous sterilization of a plurality of instruments results in the possibility of crosscontamination. Moreover, the sterilization cycle time, although less than the time required for the sterilization by solution immersion, is still relatively long, essentially because of the relatively large chamber volume.

U.S. Pat. No. 4,400,357 issued Aug. 23, 1983 to Hohmann, discloses an arrangement for chemical vapor sterilization of articles, such as dental handpieces, which would appear to overcome some of the above-mentioned problems. The patent discloses an arrangement in which the article to be sterilized is situated in an enlarged portion of a rigid vessel. A liquid reaction agent is charged into a narrow portion of the vessel which is in communication with the enlarged article-containing vessel portion. The liquid reaction agent is heated to produce a vapor which flows into the first vessel portion to sterilize the article. The first vessel portion may be designed to accept only a single article in which case the amount of liquid reaction agent required to generate the vapor is relatively small which in turn reduces the heating time required for vaporization and the overall sterilization cycle time. The patent suggests that the means for heating the liquid reaction agent may comprise a microwave radiator. In this case, the vessel is situated such that only the narrow liquid-containing vessel portion is subjected to the microwave radiation while the article to be sterilized is kept outside the radiation field which, the patent notes, avoids the formation of spark gaps at border surfaces and seams of the article which cause surface destruction. In any event, although microwave radiation is known to have beneficial sterilizing effects, the patent notes that microwave radiation will not penetrate into the seams and crevises of the article and not kill micro-organisms situated therein.

Although possibly reducing the time required for sterilization, the arrangement proposed in the patent has various drawbacks which have apparently prevented adoption and commercialization of this arrangement. For example, it requires a complicated, specially designed microwave generator adapted for positioning the vessel with only the liquid reaction agent-containing portion in the radiation field of the microwave generator with the article-containing vessel portion outside the radiation field. It requires a specially designed rigid vessel which either must be cleaned after each use to avoid cross-contamination or discarded at significant expense. The vessel must be specially designed to accommodate the size, quantity, nature and/or shape of the material being sterilized. Moreover, the sterilizing effect of the microwave radiation is not utilized since the microwave energy is used only for vaporizing the liquid reaction agent.

A good discussion of the sterilization of articles, such as dental instruments, by microwave radiation is set forth in U.S. Pat. No. 3,753,651 issued Aug. 21, 1973 to Boucher. Briefly, it is noted that sterilization by microwave radiation is due to both thermal effects, such as microwave induced heat, and non-thermal effects, which the patent suggests may affect a metabolic system distinct from that of thermal energy. It is disclosed that improved surface sterilization results are obtained when the articles are subjected to microwave radiation while situated in a humid atmosphere, i.e., an atmosphere having a relative humidity of at least 50% or supersaturated with water or saline solution. To this end, the articles to be sterilized are placed on trays which are situated in a rigid, microwave-transparent container having a known volume, along with a quantity of water or saline solution determined by the container volume so as to be sufficient when vaporized to increase the humidity of the atmosphere within the container to the desired value. After placing the articles to be sterilized and the water or saline solution into the container, the container is sealed with a lid and then placed within the cavity of a microwave generator and subjected to microwave radiation. The electro-magnetic energy penetrates through the container walls to evaporate the water or saline solution to produce the desired humidity, and at the same time, proceeds to sterilize the surface of the article by the thermal and non-thermal effects discussed above. It is indicated that this procedure results in reduced cycle time for effective sterilization compared to dry heat or steam sterilizing methods and that the localized arcing (sparking) which usually occurs when metallic objects are irradiated by microwave radiation is practically eliminated in the moist atmosphere.

The patent also points out that the container can be filled with any gas to constitute the atmosphere to be humidified. For example, it is suggested that a gas or vapor sterilant can be introduced into the container through valves provided in the container walls to take advantage of their chemical sterilizing effects, although care should be taken to avoid heating the article being sterilized to a point where it reaches the ignition or explosion point of the gas, The arrangement proposed in U.S. Pat. No. 3,753,651 has drawbacks which have apparently prevented it from being adopted on a practical basis. For example, as noted in the above-discussed U.S. Pat. No. 4,400,357, only surface sterilization is achieved by microwave irradiation and micro-organisms present on surfaces located within the seams and crevices of the article will not be killed, especially if blood and salivary protein are deposited on those surfaces. This is true regardless of whether the container is initially filled with a gas sterilant as suggested in the patent. The procedure requires a specially designed gas-tight rigid container having a known, fixed volume. The container must be sterilized after each use or discarded, in which case considerable expense is incurred especially where valves are provided in the container walls as discussed above. To provide a truly gas-tight condition, it is necessary to use materials, such as for gaskets and the like, which are not entirely transparent to microwaves. Moveover, the relatively large volume of the container which is necessary to accommodate the articles to be sterilized in turn requires a relatively large volume of water or saline solution to achieve the desired humidity. This results in an increase in the time required for the evaporation of the water or saline solution thereby increasing the overall sterilization cycle time.

SUMMARY OF THE INVENTION

It is an object of the present invention to provide new and improved methods and apparatus for sterilizing material including articles such as dental and medical instruments.

Another object of the present invention is to provide new and improved methods and apparatus for sterilizing material in a rapid manner.

Still another object of the present invention is to provide new and improved methods and apparatus for rapidly sterilizing material of various sizes, shapes and/or in various quantities.

Another object of the present invention is to provide new and improved methods and apparatus for chemical vapor sterilization of such material.

Still another object of the present invention is to provide new and improved methods and apparatus for obtaining the advantages of both chemical vapor and microwave sterilization techniques without the disadvantages noted above.

A further object of the present invention is to provide new and improved methods and apparatus for sterilizing metallic material, such as one or more metallic articles, including dental instruments and instruments having sharp edges and points, in a microwave radiation field without sparking or arcing.

Yet another object of the present invention is to provide new and improved methods and apparatus for effectively sterilizing material, such as medical and dental articles, using simple, readily available material and equipment and with a cycle time which is significantly reduced relative to prior art arrangements.

Briefly, in accordance with the present invention, these and other objects are attained by providing an arrangement wherein material, such as an article to be sterilized, is situated within a collapsible pouch formed of flexible sheet material which is vapor-impermeable. The collapsible pouch has an opening which permits insertion of the material into the pouch, the opening being sealable by the user to retain the article in the pouch and to prevent the loss of vapor therefrom. A predetermined quantity of liquid sterilant solution is introduced into the pouch along with the article whereupon the opening is sealed to form a gas-tight assembly. The liquid sterilant is then heated by any suitable means until it vaporizes. In accordance with the invention, the quantity of liquid sterilant solution introduced into the collapsible pouch is sufficient so that upon vaporization, an overpressure is created within the pouch. That the required overpressure has been achieved is visually apparent according to the invention by observation of the walls of the pouch during vaporization of the liquid sterilant solution, the walls flexing outwardly from their initial collapsed condition under the forces of the increasing internal pressure and reaching a fully distended condition upon the internal pressure reaching the required overpressure. The hot sterilant vapor contacts the surfaces of the article under pressure penetrating into the narrow seams and crevices thereof. The article is allowed to remain in the atmosphere of the hot sterilant vapor under pressure for a certain time whereupon it is effectively sterilized.

In one embodiment of the invention, particularly suited for the sterilization of medical instruments such as dental handpieces, after introducing the handpiece and liquid sterilant solution into the pouch and sealing the opening thereof, the thus-formed gas-tight assembly is placed within the cavity of a microwave radiator and subjected to microwave irradiation. In this embodiment, the collapsible pouch is formed of sheet material which, in addition to having the above-mentioned characteristics, is also transparent to microwaves. The liquid sterilant solution is vaporized under the thermal effects of the microwave radiation producing a hot sterilant vapor atmosphere under pressure as described above. At the same time, the handpiece is subjected to microwave radiation. Sterilization of the handpiece is therefore achieved by the thermal and non-thermal effects of microwave radiation as well as by chemical vapor treatment. The combined microwave and chemical vapor sterilization achieves effective and complete sterilization of the dental handpiece in significantly less time than has been possible heretofore. It is noteworthy that, surprisingly, no arcing occurs, despite microwave irradiation, in the course of sterilization of a single dental handpiece according to this procedure.

It is advantageous to utilize microwave energy for vaporizing the liquid sterilant solution within the collapsible pouch in the chemical vapor sterilization technique of the invention due to efficiency and the ready availability of microwave generators. As described above, the combined sterilizing effects of microwave irradiation and chemical vapor can be utilized in the sterilizing of a single dental handpiece according to the invention without the risk of arcing or sparking. However, it would not be possible to sterilize material comprising a plurality of metallic elements, such as a plurality of handpieces or other instruments within the same collapsible pouch in this manner without risking the possibility of arcing or sparking. Indeed, chemical vapor sterilization according to the invention of even a single pointed instrument, such as a dental explorer, may result in arcing where the instrument is subjected to microwave radiation used to heat and vaporize the liquid sterilant solution in the gas-tight assembly.

In accordance with another aspect of the invention, the simultaneous chemical vapor sterilization of a plurality of elements, such as a plurality of dental handpieces and/or one or more pointed instruments, situated in the same collapsible pouch, can be accomplished utilizing microwave energy to vaporize the liquid sterilant solution and without the risk of arcing or sparking by substantially surrounding the instrument o instruments by shielding means for preventing the transmission of microwave radiation while maintaining the instrument or instruments in communication with the ambient atmosphere. The pouch containing the shielded instruments and liquid sterilant is sealed to form a gas-tight assembly whereupon the sterilization procedure may proceed by subjecting the gas-tight assembly to microwave irradiation to produce the hot sterilant vapor as described above. The shielding means eliminates the risk of any sparking or arcing even for instruments having sharp points and edges. The hot chemical vapor atmosphere under pressure communicates with the one or more instruments to sterilize the same.

The shielding means may include a holder member, separate from or integrated with the pouch, defining an interior which is surrounded by microwave electromagnetic radiation shield material. The shielding means may also comprise a holder member which itself is formed of microwave electromagnetic radiation shield material. Alternatively, a portion of the area of the sheet material forming the collapsible pouch itself may be provided with shielding so that the shielded area surrounds an interior portion of the pouch which is thereby shielded from microwave electromagnetic radiation. The instruments to be sterilized are situated within the shielded interior portion of the pouch while the liquid sterilant solution is disposed in an unshielded interior portion to permit vaporization by microwave irradiation. The pouch is preferably positioned so that its shielded interior portion is elevated with respect to the unshielded interior portion so that any sterilant vapor that condenses in the shielded interior portion will tend to flow under gravity into the unshielded interior portion where it is reheated and re-vaporized.

According to another aspect of the invention, the collapsible pouch preferably is formed as the first step in the procedure from a section of an elongate tubular web of suitable plastic sheet material, e.g. a pair of overlying sheets presealed along their outer edge margins, and using suitable hot-wire sealing apparatus. In this manner, the size of the pouch can be "customized" for the size, shape nature and/or quantity of the particular material being sterilized.

DESCRIPTION OF THE DRAWINGS

A more complete appreciation of the present invention and many of the attendant advantages thereof will be readily understood by reference to the following detailed description when considered in connection with the accompanying drawings in which.

DETAILED DESCRIPTION OF THE PREFERRED EMBODIMENTS

Although the invention is described below in the context of sterilizing articles such as dental and medical instruments, persons skilled in the art will readily understand the applicability of the invention to the sterilizing of other materials, such as bulk particulate material, medical waste material, etc.

Figure 1:
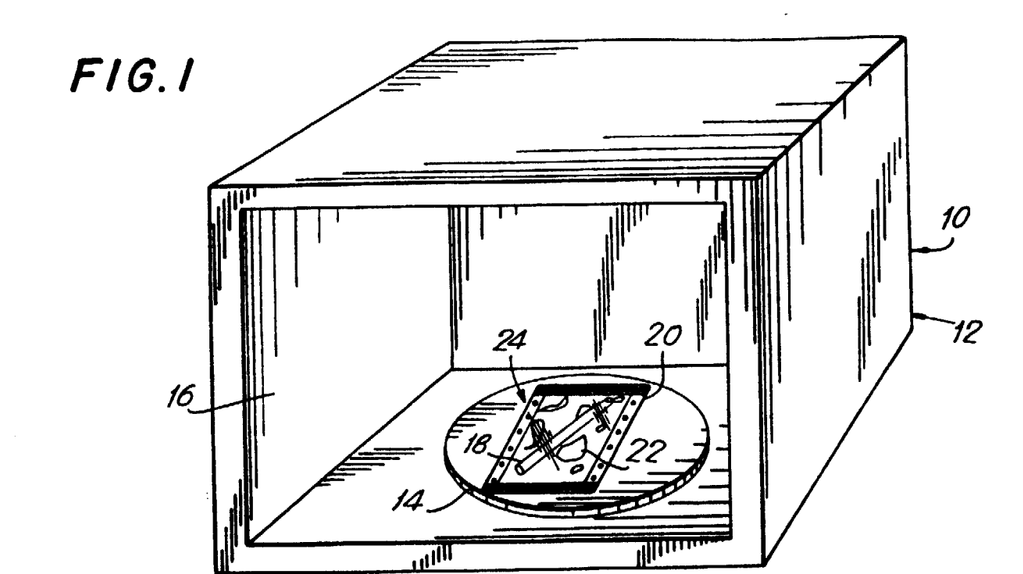
FIG. 1 is an orthoganal view of apparatus in accordance with the invention.
Figure 2:
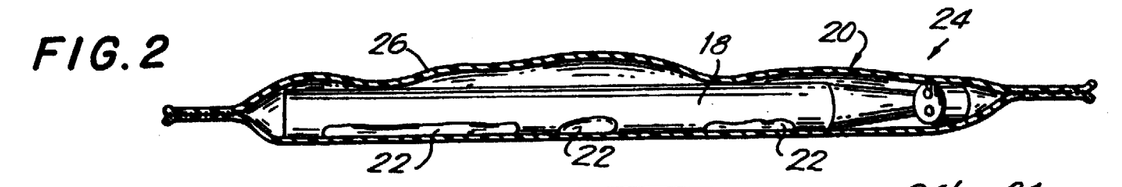
FIG. 2 is a sectional view taken along line 2—2 of FIG. 1 of a dental handpiece and liquid sterilant solution within a sealed collapsible pouch forming a gas-tight assembly.
Figure 3:
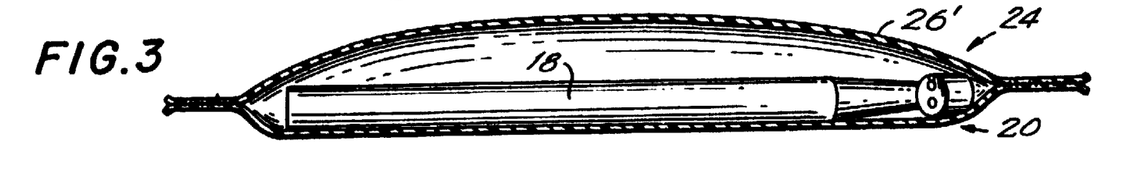
FIG. 3 is a sectional view of the gas-tight assembly shown in FIG. 2 after vaporization of the liquid sterilant solution.

Referring now to the drawings wherein like reference characters designate identical or corresponding parts throughout the several views, and more particularly to FIGS. 1-3, apparatus in accordance with the invention, generally designated 10, comprises a microwave generator, similar to conventional microwave ovens and schematically shown at 12, having a rotating table 14 located within the microwave cavity 16. A dental handpiece 18 to be sterilized is situated within a sealed, flexible or collapsible pouch 20 along with a predetermined quantity of liquid sterilant solution 22 to form a gas-tight assembly 24. The collapsible pouch 20 is designed with minimal volume preferably sufficient to accommodate only a single dental handpiece and is formed of sheet material which is transparent to microwave radiation and impermeable to the vapor of the liquid sterilant solution. In a preferred embodiment, the liquid sterilant solution comprises 2 ml. of glutaraldehyde solution and the pouch 20 is formed of sheet material having a thickness of about 2 mils and comprising a laminate of polyester and polyethylene. A predetermined amount of liquid sterilant solution 22 is introduced through an opening into the pouch 20 along with the dental handpiece 18 whereupon the opening is sealed to form the gas-tight assembly 24. The gas-tight assembly 24 comprising the collapsible pouch in which the dental handpiece 18 and liquid sterilant solution 22 is placed on the rotating table 14 within the cavity 16 of microwave generator 12 and subjected to microwave irradiation. As the microwave radiation continues, the liquid sterilant solution 22 is vaporized under the thermal effects of the microwave radiation producing a hot sterilant vapor. In accordance with the invention the quantity of liquid sterilant introduced into the collapsible pouch is sufficient so that upon vaporization, an overpressure is created within the pouch 20. That the required overpressure has been achieved is visually apparent according to the invention by observation of the walls 26 of pouch 20 which flex outwardly from their initially collapsed condition (FIG. 2) under the forces of the increasing internal pressure and reach a fully distended condition, designated 26' in FIG. 3, upon the internal pressure reaching the minimum or lower overpressure requirement. The hot sterilant vapor contacts the surfaces of the dental handpiece 18 under pressure penetrating into the narrow seams and crevices thereof. At the same time, the dental handpiece 18 is subjected to microwave irradiation. The microwave irradiation is continued for a certain time with the dental handpiece in the radiation field and in the atmosphere of the hot sterilant vapor under pressure until the handpiece has been sterilized. Sterilization of the handpiece 18 is therefore achieved by the thermal and non-thermal effects of the microwave radiation as well as by chemical vapor treatment.

Tests using a conventional, commercially available 500 watt microwave oven and the arrangement described above have shown that a dental handpiece contaminated with bacterial spores, in particular spores of Bacillus-Stearothermophilus, was effectively sterilized, i.e., all of the spores were killed, in only five minutes. It will be appreciated that spores of this bacillus are extremely difficult to kill and are generally used to test sterility effectiveness of steam autoclaves. No arcing or sparking of the handpiece caused by microwave radiation was observed when the handpiece was so irradiated in the atmosphere of the hot sterilant vapor under pressure.

The rotating table 14 is utilized in order to obtain a uniform irradiation of the gas-tight assembly 24. Of course, this can be dispensed with if the particular microwave radiator employed provides a uniform radiation field within the cavity.

Figure 4:
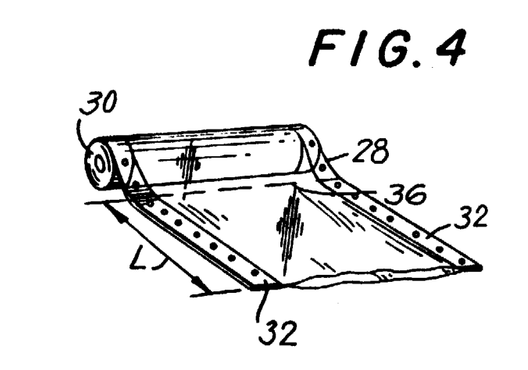
FIG. 4 is a perspective view of a roll of two-ply tubular web material used for forming a collapsible pouch.
Figure 5:
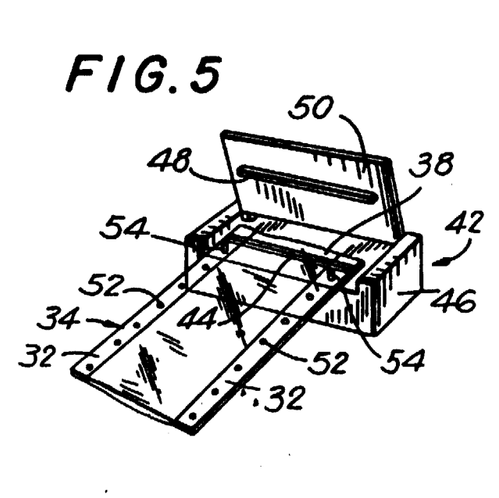
FIG. 5 is a perspective view of hot-wire sealing apparatus in use forming a collapsible pouch from the two-ply tubular web material shown in FIG. 3.

It is desirable to minimize the volume of the collapsible pouch 20 to reduce sterilization cycle time. Since different articles to be sterilized have different geometries, a preferred construction of pouch 20 will permit a "custom design" by the practitioner or his staff for a particular instrument for mimimizing the internal volume of the gas-tight assembly. In this connection, referring to FIGS. 4–6, the pouch 20 is formed from 2-ply web material 28 of constant width, preferably maintained and made available to the practitioner in the form of a roll 30. The web material 28 comprises a pair of overlying elongate sheets of polyester-polyethylene laminate whose outer edge margins 38 have been previously sealed to each other to form a tubular construction. A section 34 of the tubular web material 28 is cut from roll 30 along the line 36, the section having a length L which is somewhat greater than that required to accommodate the instrument, namely, the dental handpiece 18, to be sterilized. One of the open ends 38 of the web material section 34 is sealed by fusing the overlying sheets to each other along a transverse seal line 40 by a hot-wire sealing apparatus 42 (FIG. 5). The seal apparatus 42 comprises a fixed, heated resistance wire 44 mounted on and extending across a housing 46 and a counter-member 48 formed of a rubber-type material fixed to a cover member 50 pivotally connected to housing 46 in a position so as to come into registering alignment with wire 44 when cover member 50 is pivoted to its closed position. A series of transversly aligned perforations 52 are formed through the sealed outer edge margins 32 of the web 28 and pair of locating pegs 54 spaced from each other by a distance equal to the distance between each pair of transversely aligned perforations 52 are provided in front of resistance wire 44.

The construction of the gas-tight unit 24 proceeds as follows. After cutting tubular web section 34 from roll 30, a pair of transversely aligned perforations 52 proximate to end 38 are located over the pegs 54 such that an end region of the tubular web section 34 overlies the heated resistance wire 44. The cover member 50 of apparatus 42 is closed whereby the counter-member 48 urges the overlying sheets of tubular web 28 against each other and against the heated resistance wire 44 whereupon the sheets are fused to each other to form the transverse seal line 40 and thereby the collapsible pouch 20. The dental handpiece 18 and about 2 ml of the liquid glutaraldehyde sterilant solution 22 are introduced into pouch 20 through opening 56. The opening 56 is then sealed using the hot-wire sealing apparatus 42 in the same manner as described above to form a second transverse seal line 58 (shown in phantom in FIG. 6) proximate to the end 60 of section 34 thereby forming the sealed, gas-tight assembly 24.

Figure 6:
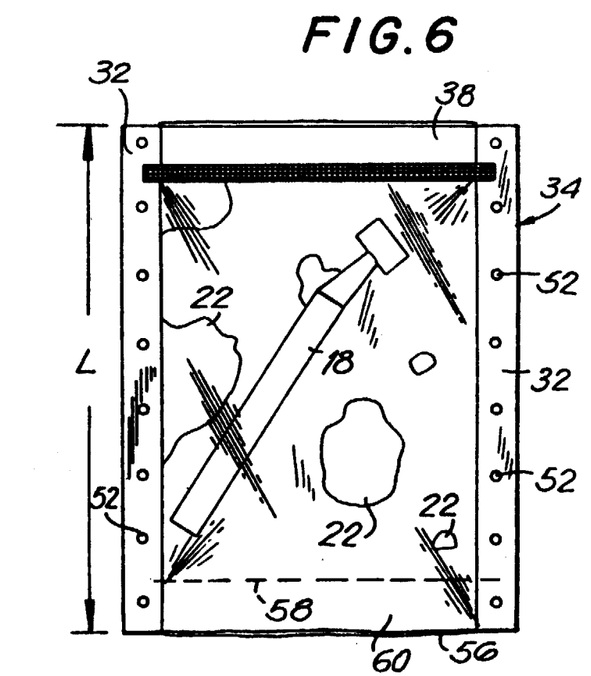
FIG. 6 is a top plan view of a pouch-forming section of the two-ply tubular web material, one side of which has been sealed and into the opening of which a dental handpiece and liquid sterilant solution have been introduced.

The above described arrangement for constructing the gas-tight assembly 24 is advantageous in that it is simple and fast. Moreover, the volume of the gas-tight assembly is custom designed for the particular instrument being sterilized, on the one hand, being sufficient to accommodate the instrument, and on the other hand, being minimized to the extent possible to reduce the quantity of liquid sterilant solution required to achieve the desired internal overpressure upon vaporization, and in turn to decrease the amount of time required to vaporize the liquid sterilant solution, and, therefore, the overall sterilization cycle time. The equipment required for constructing the collapsible pouch is simple, inexpensive and readily available. The pouches are disposable after the sterilization treatment has been completed and the dental handpiece can be stored in the gas-tight assembly until its use is required. The sterilization treatment is odorless and does not cause irritation of the eyes, nose or throat. The microwave cavity 16 need not be cleaned since the sterilant vapor is contained within the gas-tight assembly 24. Importantly, the instrument 18 is completely sterilized in a very short time.

It is advantageous to utilize microwave energy for vaporizing the liquid sterilant solution within the collapsible pouch in the chemical vapor sterilization technique of the invention because of the efficiency of its thermal effects and the ready availability of microwave generators. However, although arcing is not a problem in the combined microwave and chemical vapor sterilization of a single dental handpiece, as described above, it would not normally be possible to simultaneously sterilize a plurality of instruments situated in the same collapsible pouch or even a single instrument having a sharp point or edge in the manner described above using microwave energy to vaporize the liquid sterilant solution in the gas-tight assembly without risking the potential for arcing or sparking to occur.

In accordance with another aspect of the invention, referring to FIGS. 7-18, arrangements are illustrated by which a simultaneous chemical vapor sterilization of a plurality of instruments 62 situated in the same collapsible pouch 20 is accomplished utilizing microwave energy to vaporize the liquid sterilant solution 22 without the risk of arcing or sparking. In the case of the arrangements shown in FIGS. 7-17, the instruments to be sterilized are substantially surrounded by shielding means which present a barrier to the transmission of microwave electromagnetic radiation. The instruments surrounded by the shielding means are introduced into the collapsible pouch with the liquid sterilant solution. The pouch is sealed and the gas-tight assembly is irradiated with microwave radiation to vaporize the sterilant to produce a sterilant atmosphere at an appropriate overpressure indicated by the pouch obtaining its distended configuration. The shielding means provide communication between the instruments and the ambient atmosphere so that the instruments are bathed in the vaporized sterilant atmosphere under pressure to effectively sterilize them by chemical vapor sterilization. The instruments are on the other hand shielded from the microwave radiation by the shielding means to eliminate the possibility of arcing or sparking.

Figures 7, 8, 9:
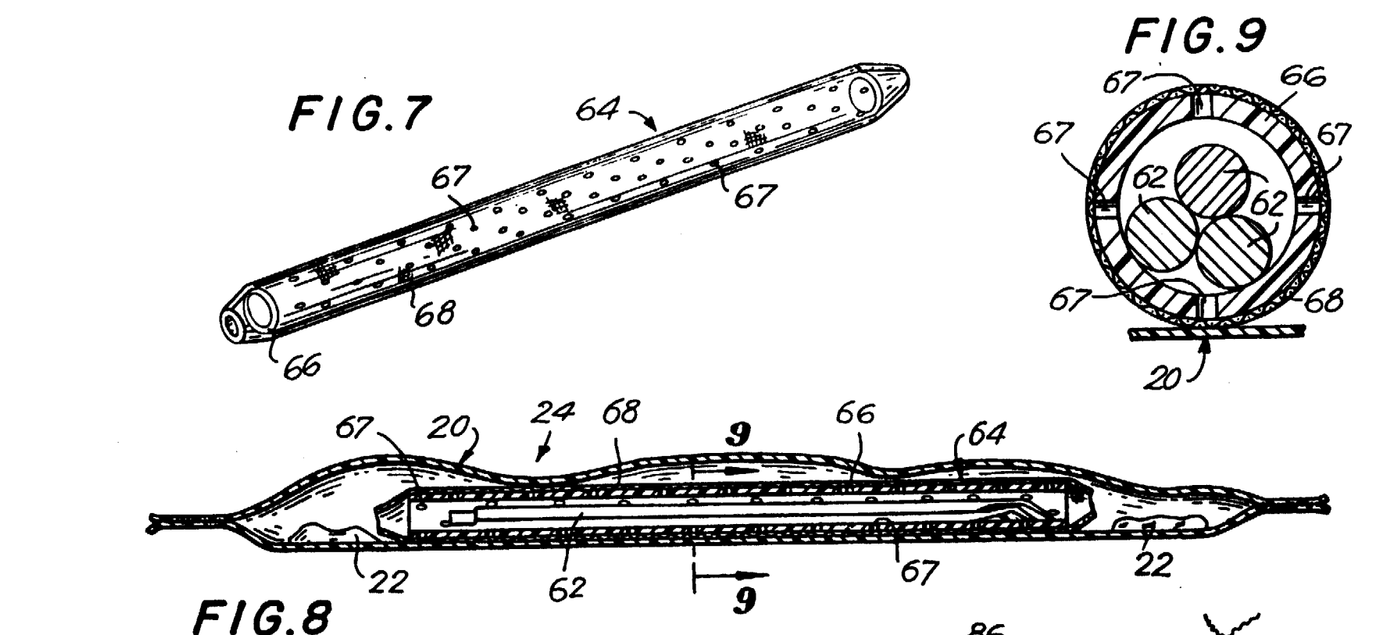
FIG. 7 is a perspective view of one embodiment of shielding means in accordance with the invention.
FIG. 8 is a sectional view of a gas-tight assembly including a collapsible pouch containing liquid sterilant solution and the shielding means surrounding a plurality of instruments to be sterilized.
FIG. 9 is a sectional view taken along line 9—9 of FIG. 8.

Referring to FIGS. 7-9, the shielding means 64 (FIG. 7) includes a holder member 66 comprising a tubular receptacle formed of an electrically insulative material, such as plastic, having a plurality of apertures 67 formed therethrough, and microwave electromagnetic radiation shield material 68 covering the outer surface of the holder member. Shield material 68 may comprise, for example, a double layered knitted mesh of tin-copper-steel wire which presents a barrier to the transmission of microwave radiation and which is available in strip form from the Tecknit Company of Cranford, N. J. under the designation EMC Shielding Tape. Thus, in this embodiment, the shielding means 64 has a tubular shape and comprises the apertured tubular holder member 66 over the outer surface of which a strip or strips of the knitted wire mesh 68 is wrapped.

In use, the instruments 62 are initially surrounded by shielding means 64 by inserting them into the interior of the tubular holder member 66 whereupon the shielding means and instruments surrounded thereby are introduced into a collapsible pouch 20 along with a quantity of liquid sterilant solution 22 whereupon the pouch is sealed to form a gas-tight assembly 24 as described above. The gas-tight assembly is irradiated by microwave radiation whereupon the liquid sterilant solution is vaporized by the thermal effects of the microwave radiation and the hot chemical vapor under pressure flows through the mesh and apertures 67 of tubular holder member 66 into contact with the surfaces of the instruments 62 to sterilize the same. No sparking or arcing occurs.

Figures 10, 14:
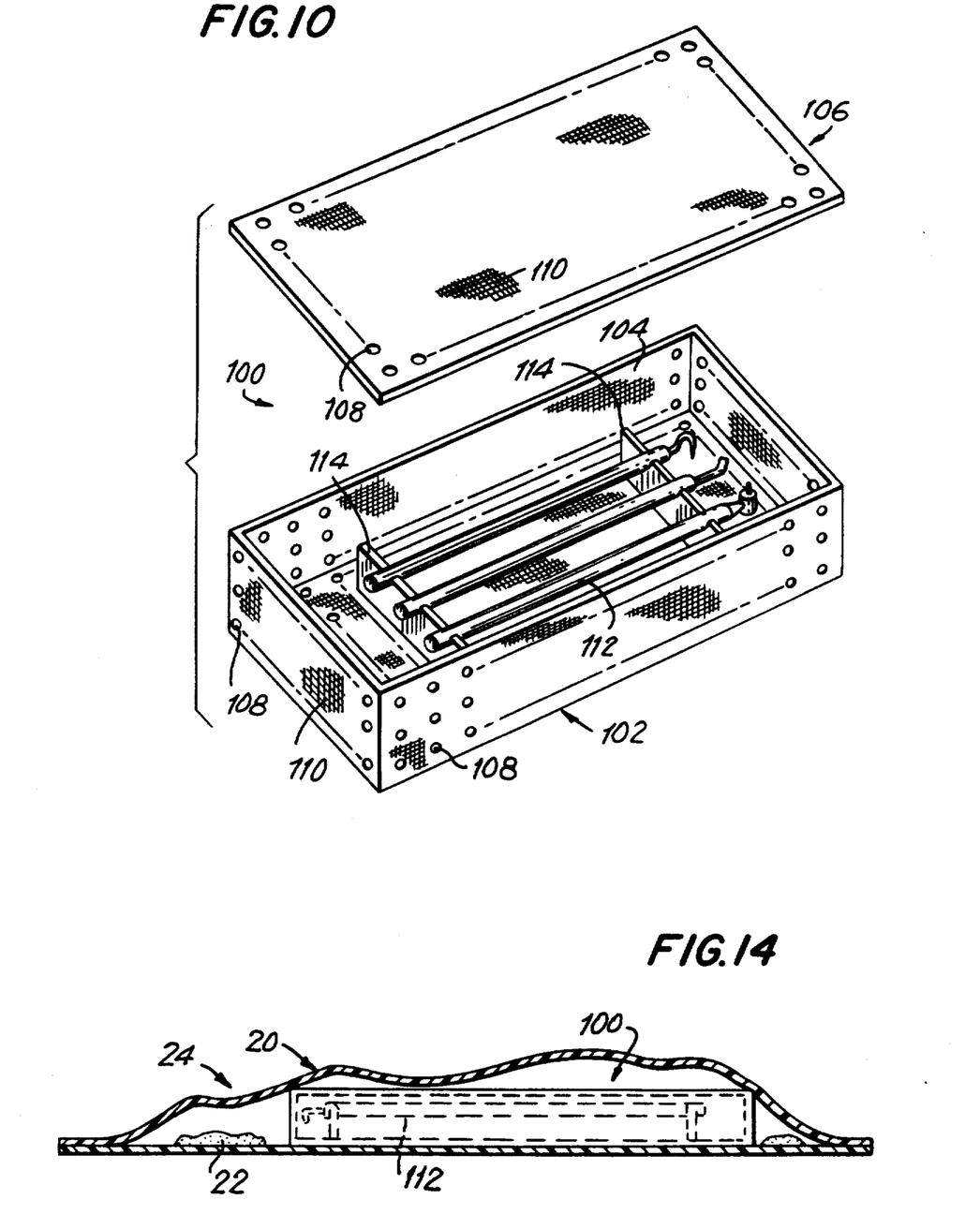
FIG. 10 is an exploded perspective view of a second embodiment of shielding means in accordance with the invention surrounding a plurality of instruments to be sterilized.
FIG. 14 is a sectional view of a gas-tight assembly including a collapsible pouch containing liquid sterilant solution and the shielding means shown in FIG. 10 surrounding a plurality of instruments to be sterilized.
Figure 11:
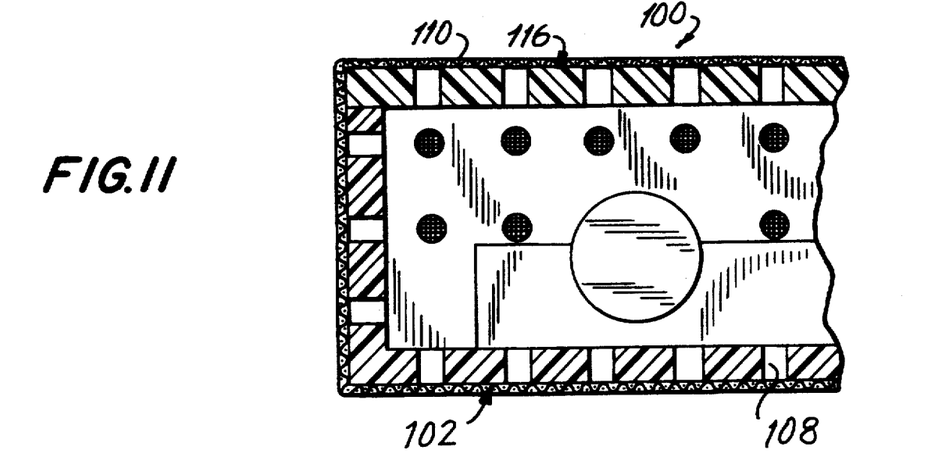
FIG. 11 is a partial sectional view of a first modification of the shielding means shown in FIG. 10.
Figure 12:
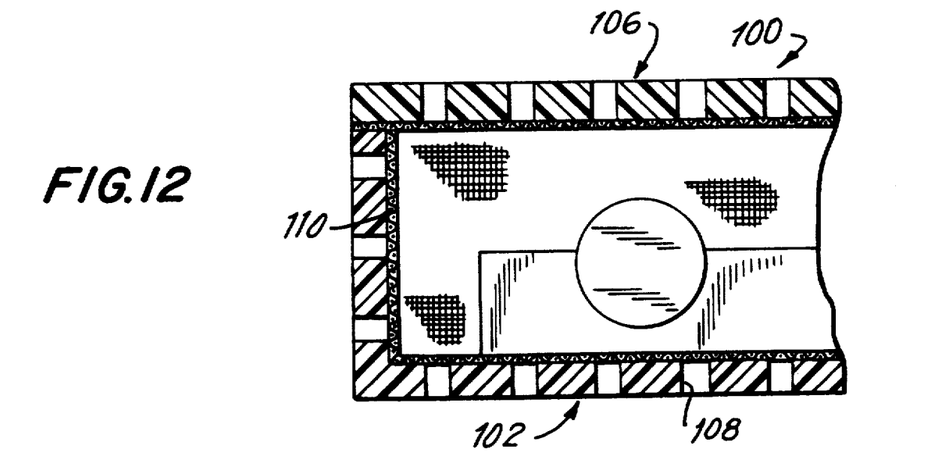
FIG. 12 is a partial sectional view of a second modification of the shielding means shown in FIG. 10.

Referring to FIGS. 10-12, another embodiment of shielding means, designated 100, includes a holder member 102 comprising a rigid box-shaped receptacle formed, for example, of plastic material, and having a removeable cover 106. Apertures 108 are formed through the walls of the receptacle 102 and cover 106. The outer surfaces of the holder member are covered by microwave electromagnetic radiation shield material 110 of the type described above, as best seen in FIG. 12. In use, instruments 112 to be sterilized are surrounded by shielding means 100 by situating them within the receptacle 102 within locating notches provided by upstanding shelves 114 and positioning the cover 106 to close the receptacle so that the instruments are surrounded by the shield material 110. The shielding means 100 and instruments 112 surrounded thereby are introduced into a collapsible pouch 20 with a quantity of liquid sterilant 22 whereupon the pouch is sealed to form a gas-tight assembly 24. The gas-tight assembly is irradiated by microwave radiation to vaporize the sterilant solution and the hot chemical vapor under pressure flows through the mesh of shield material 110 and apertures 108 of receptacle 102 and cover 106 to sterilize the instruments. The instruments 112 are shielded from the microwave radiation to eliminate the possibility of arcing or sparking. The size of the receptacle 102, although not critical, preferably is as small as possible so that it can be accommodated within a collapsible pouch the volume of which is in turn sufficiently small so that the quantity of sterilant solution required to produce the pressurized sterilant atmosphere is correspondingly minimized. In this manner, sterilization cycle time is reduced.

Figure 13:
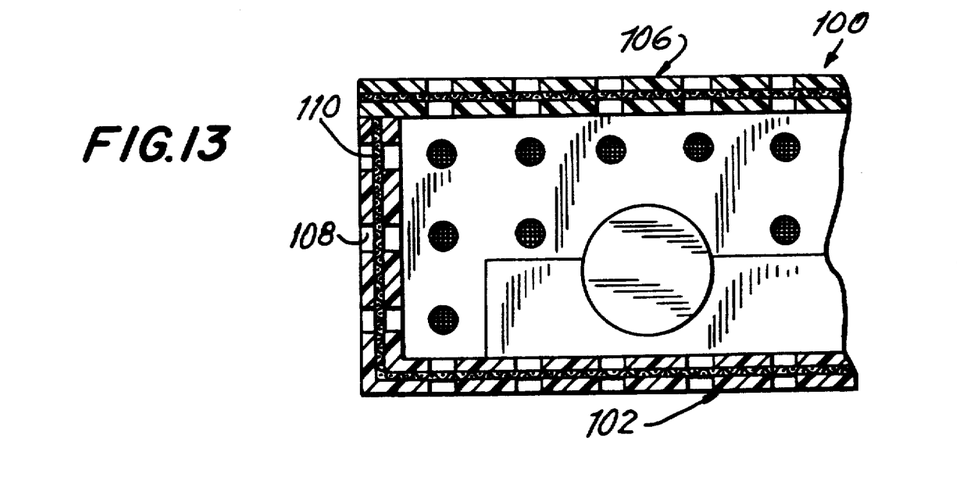
FIG. 13 is a partial sectional view of a third modification of the shielding means shown in FIG. 10.

The shield material 110 may be applied over the outer surfaces of the walls of the receptacle 102 and cover 106 as shown in FIG. 11 or, alternatively, may be applied over the inner surfaces of the receptacle walls as seen in FIG. 12, or embedded within the thickness of the receptacle walls as seen in FIG. 13.

It will be understood that the holder member 102 may be formed of materials other than plastic and the shield material may comprise materials other than wire mesh. For example, the holder member 102 of shielding means 100 shown in FIG. 10 may comprise a box-shaped receptacle formed of paper or board material having a metallic coating provided on its outer surface. This construction is advantageous in that it is sufficiently inexpensive in manufacture as to be disposable after use.

Figure 15:
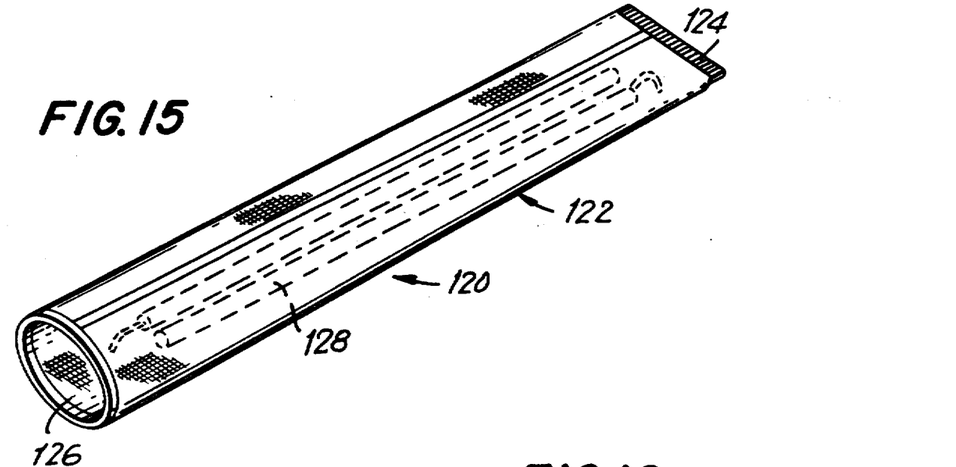
FIG. 15 is a perspective view of a third embodiment of shielding means in accordance with the invention surrounding a plurality of instruments to be sterilized.
Figure 16:
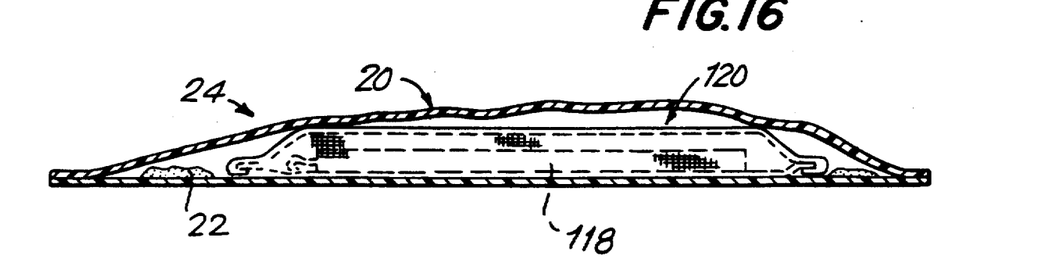
FIG. 16 is a sectional view of a gas-tight assembly including a collapsible pouch containing liquid sterilant solution and the shielding means shown in FIG. 15 surrounding a plurality of instruments to be sterilized.

Referring to FIGS. 15 and 16, another embodiment of shielding means, designated 120, comprises a holder member 122 which is itself formed of shield material, such as the knitted wire mesh shield material described above. Holder member 122 comprises a sheath of mesh shield material having one end 124 which is closed and an insertion end 126 which is closable upon insertion of one or more instruments 128 into the interior of the holder member. In use, instruments 128 are surrounded by shielding means 120 by inserting them into the sheath of holder member 122 through the insertion end 126 which is then closed by crimping. The shielding mean 120 surrounding instruments 128 is then introduced into a collapsible pouch 20 with a quantity of liquid sterilant whereupon the pouch is sealed to form a gas-tight assembly 24. The sterilant solution is vaporized by irradiating the gas-tight assembly 24 with microwave radiation and the hot chemical vapor under pressure flows through the mesh of the holder member to sterilize the instruments. The instruments are themselves shielded from the microwave radiation to eliminate the possibility of arcing or sparking.

Figure 17:
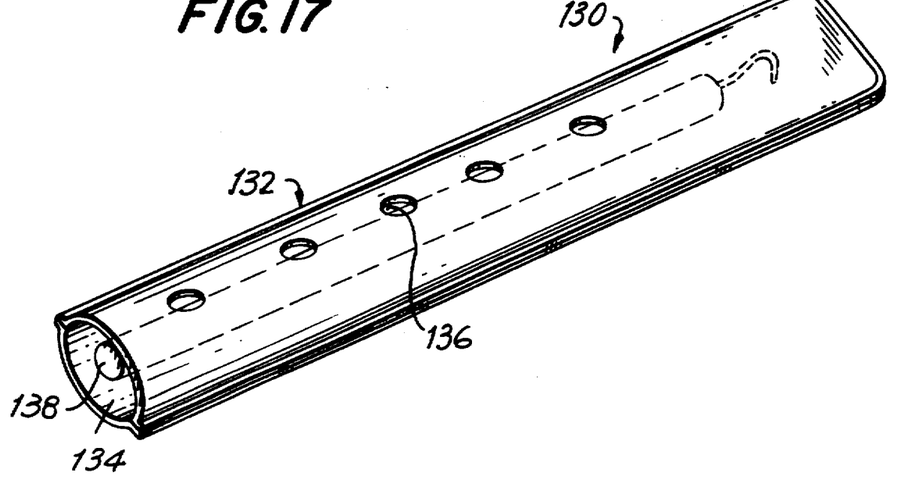
FIG. 17 is a perspective view of a fourth embodiment of shielding means in accordance with the invention surrounding an instrument to be sterilized.

Referring now to FIG. 17, another embodiment of shielding means, designated 130, also comprises a holder member 132 in the form of a sheath which is itself formed of shield material. In particular, the holder member 132 is formed of a metallic foil material, such as aluminum foil, having an open insertion end 134. The metal foil has perforations 136 formed therethrough to provide communication between the interior of the holder member 132 and the ambient atmosphere. The shielding means 130 is used in essentially the same manner as described above. At least one instrument 138 to be sterilized is surrounded by the shielding means 130 by inserting it into the holder member 132 through the insertion end 134 thereof which is then closed by crimping. The shielding means 130 surrounding instrument 138 is introduced into a collapsible pouch along with liquid sterilant solution. Sterilization proceeds as described above.

It is understood that the holder member 132 may be formed of shield materials other than as described above. For example, the holder member may be formed of plastic film or paper provided with a metallic coating or a metallic laminate. It is also noted that the perforations 136 should be of a size less than a certain dimension to ensure that microwave radiation cannot pass through them. For example, if the perforations are circular and have diameters less than about one-quarter the wavelength of the microwave radiation, the radiation should for practical purposes be substantially prevented from passing through them.

Figure 18A:
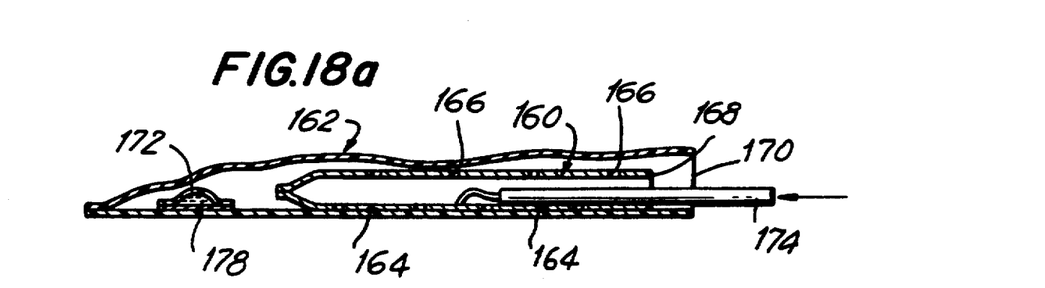
FIG. 18a is a sectional view of an embodiment wherein the shielding means illustrated in FIG. 17 is integrated with a collapsible pouch and illustrating the insertion of an instrument to be sterilized simultaneously into both the shielding means and pouch.
Figure 18B:
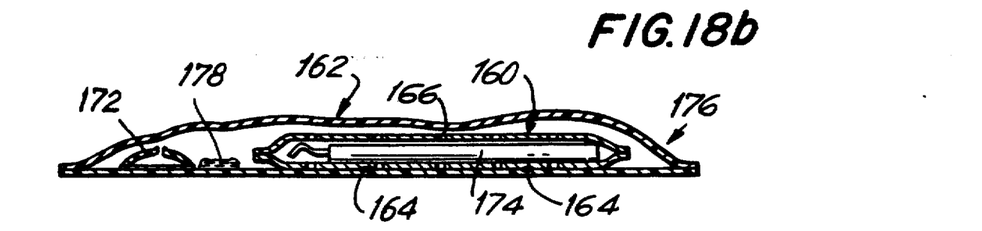
FIG. 18b is a view similar to FIG. 18a illustrating a gas-tight assembly formed after the instrument is fully inserted and the pouch sealed.

Referring now to FIGS. 18a and 18b, an embodiment of the invention is shown wherein shielding means are integrated with a collapsible pouch to form a unitary assembly. More particularly, shielding means in the form of a sheath-like holder member 160 are situated within the interior of a collapsible pouch 162 of the type described above and affixed to the inner surface thereof such as by adhesive tacking at 164. Holder member 160 is formed of a metallized substrate, such as aluminized paper, and has substantially the same construction as that shown in FIG. 17 including perforations 166 and an open insertion end 168. The holder member 160 is fixed within the pouch 162 in a position such that the open insertion end is situated adjacent to and recessed a small distance inwardly from the open end 170 of pouch 162. A capsule or sachet 172 containing an appropriate quantity of liquid sterilant solution is also predisposed within pouch 162.

In use, referring to FIG. 18a, an instrument 174 to be sterilized is inserted into pouch 162 through its open end 170 and, at the same time, into the interior of the holder member 160 of the shielding means through the insertion end 168. The insertion end of holder member 168 is closed and pouch 162 is sealed to form a gas-tight assembly 176 shown in FIG. 18b. At this time the liquid sterilent solution 178 is released from sachet 172 whereupon the assembly 176 is irradiated with microwave electromagnetic radiation to vaporize the sterilant.

The assembly comprising the collapsible pouch 162 and holder member 160 fixed thereto may advantageously be constructed and sold as a single unit, either with or without the sachet of liquid sterilant solution predisposed therein. The assembly is preferably constructed so as to be disposable after a single use.

Figure 19:
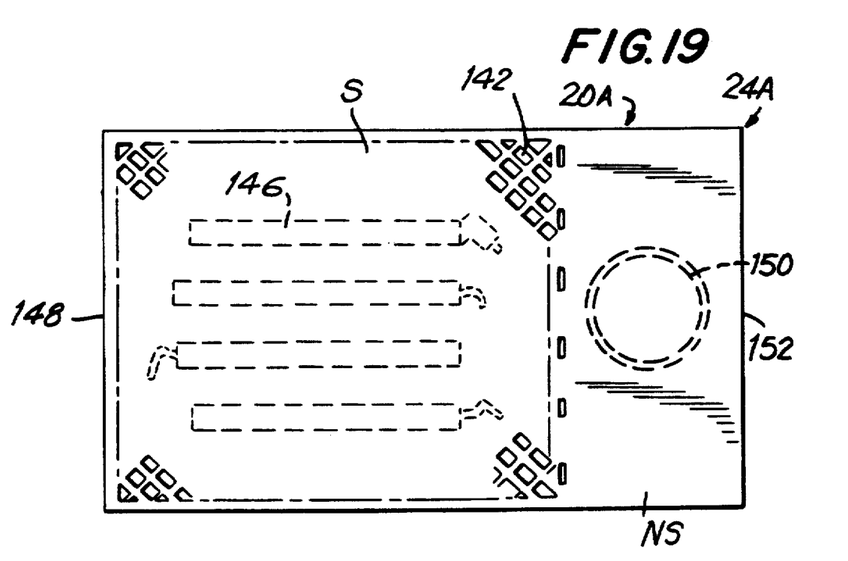
FIG. 19 is a top plan view of a gas-tight assembly including a collapsible pouch wherein shielding is provided on the sheet material forming the pouch.

A somewhat different construction of an embodiment wherein shielding means are integrated with a collapsible pouch is illustrated in FIG. 19. In this embodiment, a defined portion S of the area of the sheet material of a collapsible pouch 20A of the type described above is provided with microwave electromagnetic radiation shield means while the remaining area NS of the sheet material of pouch 20A remains transparent to microwave radiation. The shield means may take the form of a metallic grid-like coating 142 deposited over the area S of the sheet material of the pouch as shown or may simply comprise a continuous or solid metallic coating. The shielded area S surrounds an interior portion of the collapsible pouch which is thereby shielded from microwave radiation while the non-shielded area NS surrounds an interior portion of the pouch which is not so shielded. A transversely extending series of spaced heat seals 144 join opposed regions of the sheet material of pouch 20A to separate the shielded interior portion of pouch 20A from the non-shielded interior portion. The shielded and non-shielded interior portions communicate with each other through the voids between the heat seals 144. The shielded interior portion of pouch 20A is of sufficient extent to surround instruments 146 to be sterilized.

In use, the instruments 146 are inserted into the shielded interior portion of pouch 20A through a first open end which is then sealed at 148. Liquid sterilant solution, preferably contained within a cup 150, is introduced into the non-shielded interior portion of pouch 20A through a second open end which is then sealed at 152 to form a gas-tight assembly, designated 24A. The gas-tight assembly is irradiated with microwave radiation whereby the sterilant solution in cup 150 vaporizes and the pressurized sterilant atmosphere fills the shielded interior portion of the pouch to sterilize instruments 146. The possibility of arcing or sparking is eliminated since the shielding 142 presents a barrier to the transmission of the radiation into the interior portion of the pouch in which the instruments are situated. It will be understood that it is not essential that the pouch be provided with seals 144 or that the liquid sterilant be contained within a cup so long as the instruments are substantially surrounded by shield means and the liquid sterilant is situated in a non-shielded interior portion of the pouch.

Figure 20:
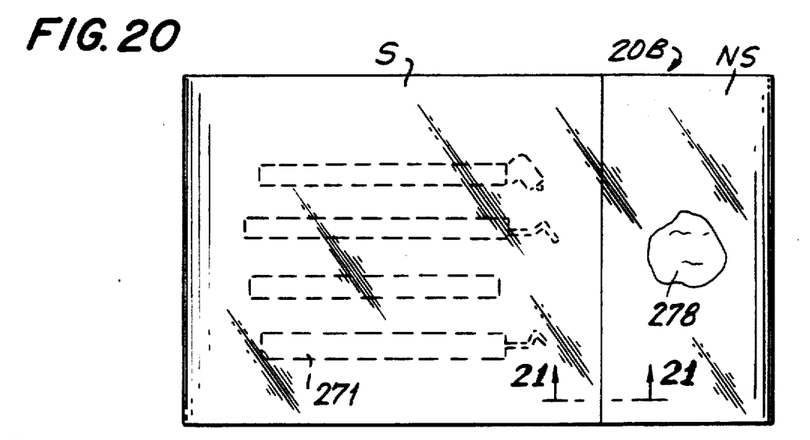
FIG. 20 is a top plan view of another embodiment of a gas-tight assembly including a collapsible pouch wherein shielding is provided on the sheet material forming the pouch.
Figure 21A:
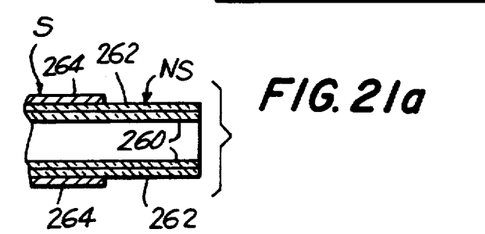
FIGS. 21a–21c are sectional views taken along line 21—21 of FIG. 20 of alternate embodiments of the construction of the collapsible pouch shown in FIG. 20.
Figure 21B:
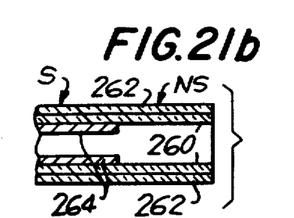
Figure 21C:
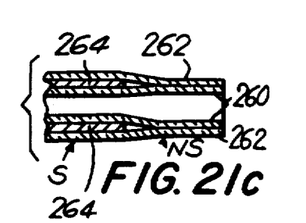

Another embodiment wherein shielding means are integrated with a collapsible pouch is illustrated in FIGS. 20 and 21. Like the embodiment illustrated in FIG. 19, electromagnetic radiation shield means cover a portion S of the sheet material of a collapsible pouch 20B while the remaining area NS of the sheet material of pouch 20B remains transparent to microwave radiation.

The sheet material of pouch 20B is a laminate having a thickness on the order of about 2 mils comprising an inner layer 260 of polyethylene or polypropylene and an outer layer 262 of a polyester material. The shield means comprises metallic foil 264, such as 35 gauge aluminum foil, covering the entire area S of pouch 20B and integrated with the laminate so as to become a part of the sheet material.

In the embodiment of FIG. 21a, the metallic foil 264 is affixed on the outer surface of outer layer 262 of the sheet material forming the top and bottom of pouch 20B. In the embodiment of FIG. 21b, the metallic foil 264 is affixed to the inner surface of inner layer 260 of the sheet material forming the top and bottom of pouch 20B. In either case, the affixation may be accomplished by appropriate adhesive. Alternatively, the metallic foil shielding material can be interposed between the inner and outer layers 260 and 262 during manufacture of the laminate as seen in FIG. 21c.

In any of the cases described above where shielding means, whether provided separately from or integrated with the pouch, define an interior portion within the collapsible pouch that is shielded from radiation, it is advantageous for the pouch to be oriented so that the shielded interior portion is elevated relative to a non-shielded interior portion. The reason is that the sterilant vapor entering the shielded interior portion tends to cool and condense on the inner surface of the sheet material and/or on the surface of the instrument. By elevating the shielded interior portion relative to the non-shielded portion, any condensation forming in the non-shielded interior portion tends to flow downwardly under gravity from the non-shielded region of the pouch into the shielded region where it is irradiated, heated and revaporized. In this manner, the concentration of the sterilant in the atmosphere is maintained relatively constant.

Figure 22:
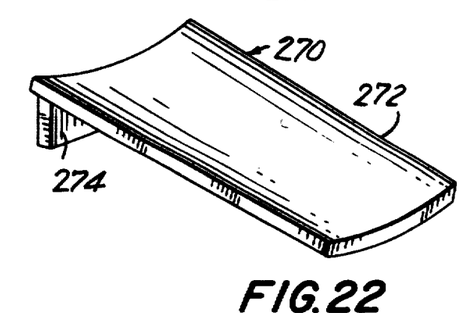
FIG. 22 is a perspective view of a device for positioning a gas-tight assembly so that its shielded interior portion is elevated with respect to an unshielded interior portion.
Figure 23:
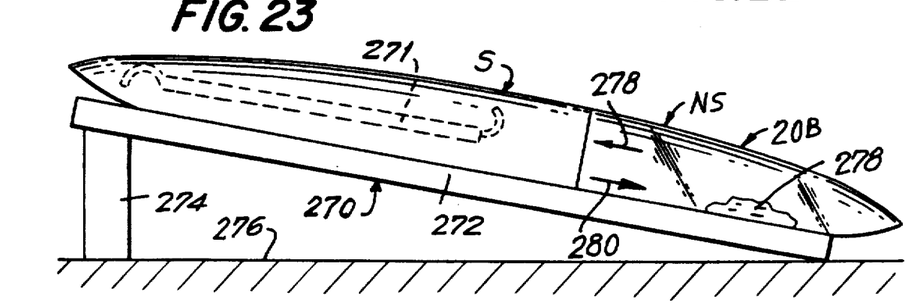
FIG. 23 is a front elevation view illustrating a gas-tight assembly positioned on a positioning device of the type shown in FIG. 22 during sterilizing.

Referring to FIGS. 22 and 23, a device 270 for positioning a gas-tight assembly of the type shown in FIG. 20 so that the shielded interior portion surrounded by the shielded area S of the sheet material is elevated with respect to the non-shielded interior portion defined by the non-shielded area NS of pouch 20B. The positioning device essentially includes an inclined platform or shelf comprising a concave platform 272 and an upstanding leg 274 affixed to one end of platform 272. The platform and leg are both formed of microwave transparent material.

In use, one or more instruments 271 are inserted into the shielded interior portion of pouch 20B through an open end, and a sachet 278 containing liquid sterilant solution is inserted into the non-shielded interior portion, whereupon the open end is sealed to form a gas-tight assembly. The gas-tight assembly is then placed on the platform 272 of positioning device 270 which has been, or is thereupon, situated on the floor 276 of a microwave cavity. The gas-tight assembly is then irradiated with microwave radiation whereupon the sterilant solution vaporizes causing the sachet 278 to burst. The sterilant vapor under pressure moves into the shielded interior portion of the pouch as schematically shown by arrow 278. Since the shielded interior pouch portion is relatively cool, some sterilant vapor may condense on the inner pouch wall or on the surface of the instruments 271. By elevating the shielded pouch interior portion relative to the unshielded portion, any condensate flows downwardly under gravity, as schematically shown by arrow 280, into the unshielded interior portion where it is irradiated by the microwave radiation and revaporized. In this manner the concentration of sterilant vapor is maintained substantially constant.

As noted above, the orientation of the gas-tight assembly in a manner to cause any sterilant solution condensate to drain into an unshielded interior pouch portion is not limited to assemblies in which the shielding means are integrated with the pouch. For example, the embodiments of the gas-tight assembly shown in FIGS. 8, 10, 16 and 18b may be advantageously oriented in a similar manner.

Figure 24:
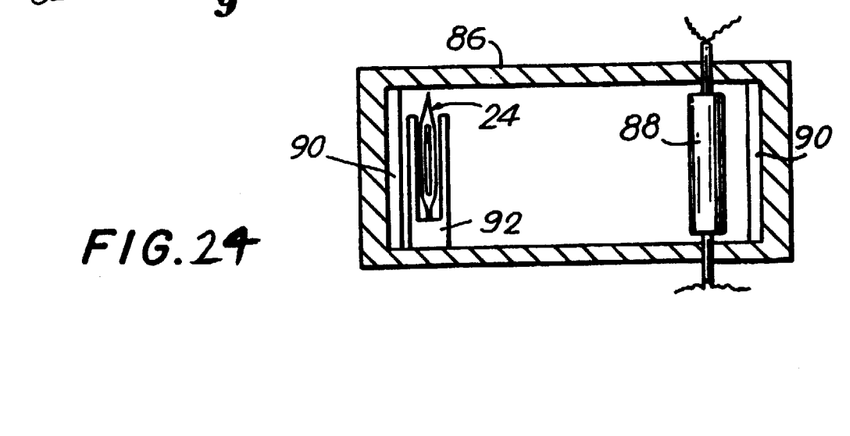
FIG. 24 is a front elevation view of another embodiment of apparatus in accordance with the invention.

It will be understood that sterilization can be accomplished according to the invention using only the chemical vapor under pressure arrangement of the invention in the absence of microwave radiation. For example, referring to FIG. 24, the gas-tight assembly 24 of FIG. 2, including a collapsible pouch in the interior of which is sealed an instrument to be sterilized and an appropriate quantity of liquid sterilant solution, is situated in the interior of an infrared radiator device 86 in which a rod-shaped infrared radiator 88 is provided. Elliptical mirrors 90 are provided within the infrared radiator device 86 defining a pair of vocal lines for the infrared radiation emitted from radiator 88. The infrared radiator 88 is positioned on the first focal line and the gas-tight assembly is situated in a simple holder device 92 at the second focal line. When the radiator 88 is activated, a high beam concentration of the infrared radiation is focused onto the gas-tight assembly 24 rapidly vaporizing the liquid sterilant solution to sterilize the instrument by chemical vapor as described above.

Obviously, numerous modifications and variations of the present invention are possible in the light of the above teachings. It is therefore to be understood that within the scope of the claims appended hereto, the invention may be practiced otherwise than as specifically disclosed herein.

What is claimed is:

1. An assembly for use in sterilizing at least one object by vapor under pressure, including:
   a collapsible pouch comprising flexible vapor-impermeable sheet material forming an interior and a sealable opening into said interior through which said at least one object can be introduced into said interior, said sheet material including a first wall portion comprising microwave electromagnetic radiation shield material substantially surrounding and defining a first interior portion of said collapsible pouch which is adapted to receive said at least one object and which is maintained substantially free from microwave electromagnetic radiation during irradiation of said pouch by microwave irradiating means, and a second wall portion comprising microwave electromagnetic radiation transparent material substantially surrounding and defining a second interior portion of said collapsible pouch which is exposed to microwave electromagnetic radiation during irradiation of said pouch by microwave irradiating means; and
   means for positioning said pouch such that said first shielded interior portion of said collapsible pouch that is substantially free of radiation during irradiation is elevated to a position that is higher than said second unshielded interior portion of said collapsible pouch which is exposed to said radiation.

2. An assembly as recited in claim 1, wherein said microwave radiation shield material of said first wall portion of said pouch extends continuously from a first end region of said pouch to a central region thereof, and said microwave electromagnetic radiation transparent material of said second wall portion extends from a second end of said pouch opposite from said first end to said central region thereof.

3. An assembly as recited in claim 1 wherein said first and second interior portions of said pouch together comprise the entire interior of said pouch.

4. An assembly as recited in claim 1 wherein said vapor-impermeable sheet material forming said pouch comprises plastic sheet material, and wherein said microwave electromagnetic radiation shield material is applied on said plastic sheet material to form said first wall portion.

5. An assembly as recited in claim 1 wherein said pouch positioning means comprise and elongate platform having leg means at an end region thereof for orienting said platform in an inclined position, said pouch adapted to be supported on said inclined platform with said first shielded interior portion elevated to a position higher than said second unshielded interior portion.

6. Apparatus for sterilizing at least one object by vapor under pressure, comprising:
   a collapsible pouch formed of flexible vapor-impermeable sheet material;
   said flexible sheet material including a first wall portion comprising microwave electromagnetic radiation shield means substantially surrounding a first interior portion of said collapsible pouch which is thereby shielded from microwave electromagnetic radiation, said sheet material of said pouch including a second wall portion comprising material transparent to microwave radiation substantially surrounding a second non-shielded interior portion of said collapsible pouch;
   said first shielded interior portion of said collapsible pouch adapted to receive said at least one object;
   said second non-shielded interior portion of said collapsible pouch adapted to receive a quantity of liquid;
   said collapsible pouch being sealable after receiving said at least one object and said liquid to form a gas-tight assembly;
   said liquid contained within said pouch being of a quantity sufficient to create an overpressure within said gas-tight assembly when vaporized, indicated by said collapsible pouch expanding to a distended condition;
   means for irradiating said gas-tight assembly with microwave electromagnetic radiation to vaporize said liquid to produce an atmosphere of hot vapor under pressure in said gas-tight assembly with said shield means presenting a barrier to transmission of substantial microwave electromagnetic radiation to said at least on object thereby preventing arcing or sparking and;
   means for positioning said gas-tight assembly during irradiation such that said first shielded interior portion of said collapsible pouch that is substantially free of said radiation is elevated to a position that is higher than said second unshielded interior portion of said collapsible pouch which is exposed to said radiation,
   whereby upon irradiating said gas-tight assembly with microwave electromagnetic radiation, said at least one object situated in said first interior portion of said pouch is substantially entirely shielded from said radiation, and said liquid situated in said second interior portion is exposed to said radiation whereupon it is heated and then vaporized thereby, whereupon the vapor moves into said first shielded interior portion of said pouch in which some of said vapor may condense whereupon the condensate then flows downwardly under gravity into said second unshielded interior portion of said pouch in which it is revaporized, whereupon said at least one object is sterilized under the effect of vapor under pressure.

7. Apparatus as recited in claim 6 wherein said shield means comprise a coating of metallic material provided on said first wall portion of said sheet material of said collapsible pouch.

8. Apparatus as recited in claim 6 wherein said collapsible pouch includes means for separating said first and second interior portions of said collapsible pouch, and means for fluidly communicating said first and second interior portions of said collapsible pouch.

9. Apparatus as recited in claim 6 wherein said gas-tight assembly positioning means comprise an elongate platform having leg means at an end region thereof for orienting said platform in an inclined position, said pouch adapted to be supported on said inclined platform with said first shielded interior portion elevated to a position higher than said second unshielded interior portion.

10. Apparatus for sterilizing at least one object by vapor under pressure, comprising:

a gas-tight collapsible pouch formed of flexible vapor-impermeable sheet material at least partially transparent to microwave electromagnetic radiation, said pouch having a sealable opening through which said at least one object can be introduced into the interior thereof;

liquid receivable within said pouch in a quantity sufficient such that when said pouch opening is sealed and said liquid is vaporized, an overpressure is created within said gas-tight pouch which causes said pouch to expand to a visually-apparent distended condition;

means for irradiating said gas-tight pouch with microwave electromagnetic radiation to vaporize said liquid to produce an atmosphere of hot vapor under pressure in said gas-tight pouch which expands said collapsible pouch to a visually-apparent distended condition;

shielding means associated with said collapsible pouch for dividing the interior of said pouch into a first shielded interior portion which is substantially free of said microwave electromagnetic radiation during irradiation of said gas-tight pouch by said irradiating means and a second unshielded interior portion which is exposed to said microwave electromagnetic radiation during irradiation of said gas-tight pouch by said irradiating means, said first interior portion being receivable of said at least one object to be sterilized and said second interior portion being receivable of said liquid, and means for positioning said gas-tight pouch during irradiation such that said first shielded interior portion of said collapsible pouch that is substantially free of said radiation is elevated to a position higher than said second unshielded interior portion of said collapsible pouch which is exposed to said radiation;

whereby upon irradiating said gas-tight pouch with microwave electromagnetic radiation, said at least one object situated in said first interior portion of said pouch is substantially entirely shielded from said radiation, and said liquid situated in said second interior portion is exposed to said radiation whereupon it is heated and then vaporized thereby, whereupon the vapor moves into said first shielded interior portion of said pouch in which some of said vapor may condense whereupon the condensate then flows downwardly under gravity into said second unshielded interior portion of said pouch in which it is revaporized, whereupon said at least one object is sterilized under the effect of vapor under pressure.

11. Apparatus as recited in claim 10 wherein said pouch positioning means comprise an elongate platform having leg means at an end region thereof for orienting said platform in an inclined position, said pouch adapted to be supported on said inclined platform with said first shielded interior portion elevated to a position higher than said second unshielded interior portion.

12. Apparatus as recited in claim 10, wherein said shielding means and said collapsible pouch comprise an integrated unit.

13. Apparatus as recited in claim 12 wherein said flexible vapor-impermeable sheet material which forms said collapsible pouch includes a first wall portion comprising microwave electromagnetic radiation shield material substantially surrounding and defining said first shielded interior portion of said collapsible pouch which is thereby maintained substantially free from microwave electromagnetic radiation during irradiation of said pouch by said irradiating means, and a second wall portion comprising microwave electromagnetic radiation transparent material substantially surrounding and defining said second unshielded interior portion of said collapsible pouch which is thereby exposed to microwave electromagnetic radiation during irradiation of said pouch by said irradiating means.

14. Apparatus as recited in claim 13 wherein said microwave radiation shield material of said first wall portion of said pouch extends continously from a first end of said pouch to a central region thereof, and said microwave electromagnetic radiation transparent material of said second wall portion of said pouch extends continuously from a second end of said pouch opposite from said first end to said central region thereof.

15. Apparatus as recited in claim 14 wherein said vapor-impermeable sheet material comprises flexible plastic sheet material, and wherein said shield material comprises a coating of metallic material provided on said plastic sheet material comprising said first wall portion of said collapsible pouch.

16. Apparatus as recited in claim 12 wherein said integrated unit comprises said shielding means situated within and fixed to said collapsible pouch.

17. Apparatus as recited in claim 16 wherein said shielding means include a holder member fixed within said collapsible pouch, said holder member defining an interior in fluid communication with the ambient atmosphere and adapted to receive said at least one object.

18. Apparatus as recited in claim 17 wherein said holder member includes a receptacle adapted to receive said at least one object, said receptacle having an insertion opening situated proximate to said pouch opening.

19. Apparatus as recited in claim 18 wherein said receptacle comprises a sheath formed of microwave electromagnetic radiation shield material.

20. Apparatus as recited in claim 10, wherein said shielding means include a holder member defining an interior in fluid communication with the ambient atmosphere and adapted to receive said at least one object.

21. Apparatus as recited in claim 20 wherein said holder member is formed of microwave electromagnetic radiation shield material.

22. Apparatus as recited in claim 21 wherein said holder member comprises a sheath formed of microwave electromagnetic radiation shield material.

23. Apparatus as recited in claim 21 wherein said microwave electromagnetic radiation shield material comprises metallic wire-mesh material.

24. Apparatus as recited in claim 21 wherein said microwave electromagnetic radiation shield material comprises metallic sheet material.

25. Apparatus as recited in claim 21 wherein said microwave electromagnetic radiation shield material comprises metallic foil material.

26. Apparatus as recited in claim 21 wherein said microwave electromagnetic radiation shield material comprises non-metallic sheet material having a metallic coating.

27. Apparatus as recited in claim 20 wherein said holder member includes a receptacle adapted to receive said at least one object and having at least one wall defining said interior, said wall having inner and outer surfaces, and wherein said shielding means further includes microwave electromagnetic radiation shield material surrounding said interior of said receptacle.

28. Apparatus as recited in claim 27 wherein said shield material is situated over said outer surface of said at least one receptacle wall.

29. Apparatus as recited in claim 27 wherein said shield material is situated over said inner surface of said at least one receptacle wall.

30. Apparatus as recited in claim 27 wherein said shield material is embedded within said at least one receptacle wall.

31. Apparatus as recited in claim 27 wherein said receptacle comprises a tubular member.

32. Apparatus as recited in claim 27 wherein said receptacle comprises a rigid box-like member.

33. Apparatus as recited in claim 27 wherein said receptacle includes means for positioning said at least one object within said interior thereof.

34. Apparatus as recited in claim 27 wherein said microwave electromagnetic radiation shield material comprises metallic wire-mesh material.

35. Apparatus as recited in claim 27 wherein said microwave electromagnetic radiation shield material comprises a metallic coating applied on at least one of said inner and outer surfaces of said at least one receptacle wall.

* * * * *